IIIIII US008822640B2

(12) United States Patent
Wong et al.

(10) Patent No.: US 8,822,640 B2
(45) Date of Patent: Sep. 2, 2014

(54) TETRAMERIC STREPTAVIDIN MUTEIN WITH REVERSIBLE BIOTIN BINDING CAPABILITY

(75) Inventors: Sui-Lam Wong, Calgary (CA); Sau-Ching Wu, Calgary (CA); Isabelle Barrette-Ng, Calgary (CA); Ken Ng, Calgary (CA)

(73) Assignee: UTI Limited Partnership, Calgary (CA)

( * ) Notice: Subject to any disclaimer, the term of this patent is extended or adjusted under 35 U.S.C. 154(b) by 347 days.

(21) Appl. No.: 13/272,922

(22) Filed: Oct. 13, 2011

(65) Prior Publication Data

US 2013/0035471 A1 Feb. 7, 2013

Related U.S. Application Data

(60) Provisional application No. 61/514,325, filed on Aug. 2, 2011.

(51) Int. Cl.
| | |
|---|---|
| *C07K 14/36* | (2006.01) |
| *C12N 15/31* | (2006.01) |
| *C07K 1/22* | (2006.01) |
| *C07K 14/32* | (2006.01) |

(52) U.S. Cl.
CPC .. *C07K 14/32* (2013.01); *C07K 1/22* (2013.01)
USPC ........... 530/350; 536/23.7; 530/344; 530/413

(58) Field of Classification Search
CPC ...................................................... C07K 14/36
See application file for complete search history.

(56) References Cited

U.S. PATENT DOCUMENTS 6,312,916 B1 11/2001 Kopetzki et al.

OTHER PUBLICATIONS

Reznik et al. "Streptavidins with intersubunit crosslinks have enhanced stability," Nature Biotechnology, vol. 14, Aug. 1996, pp. 1007-1011.*
Bulmus et al., "Site-specific polymer-streptavidin bioconjugate for pH-controlled binding and triggered release of biotin," *Bioconjugate Chemistry*, 11:78-83, 2000.
Chilkoti et al., "Engineered chimeric streptavidin tetramers as novel tools for bioseparations and drug delivery," *Biotechnology*, 13:1198-1204, 1995.

Chivers et al., "A streptavidin variant with slower biotin dissociation and increased mechanostability," *Nat. Methods*, 7(5):391-393, 2010.
Chivers et al., "How the biotin-streptavidin interaction was made even stronger: investigation via crystallography and a chimaeric tetramer," *Biochem. J.*, 435(1):55-63, 2011.
Freitag et al., "Structural studies of binding site tryptophan mutants in the high-affinity streptavidin-biotin complex," *J. Mol. Biol.*, 279(1):211-221, 1998.
Freitag et al., "Structural studies of the streptavidin binding loop," *Protein Sci.*, 6(6): 1157-1166, 1997.
O'Sullivan et al., "Development of a tetrameric streptavidin mutein with reversible biotin binding capability: engineering a mobile loop as an exit door for biotin," *PLoS One*, 7(4):e35203, 2012.
PCT International Search Report and Written Opinion issued in International Application No. PCT/IB2012/001953, mailed Feb. 11, 2013.
PCT International Search Report and Written Opinion issued in International Application No. PCT/IB2012/002212, mailed Mar. 19, 2013.
Qureshi et al., "Development and characterization of a series of soluble tetrameric and monomeric streptavidin muteins with differential biotin binding affinities," *J. Biol. Chem.*, 276(46):46422-46428, 2001.
Reznick et al., "Streptavidins with intersubunit crosslinks have enhanced stability," *Nat Biotechnol.*, 14(8):1007-1011, 1996.
Sano and Cantor, "Intersubunit contacts made by tryptophan 120 with biotn are essential for both strong biotin binding and biotin-induced tighter subunit association of streptavidin," *Proc. Natl. Acad. Sci. USA*, 92:3180-3184, 1995.
Wu and Wong, "Engineering soluble monomeric streptavidin with reversible biotin binding capability," *J. Biol. Chem.*, 280(24):23225-23231, 2005.
Wu and Wong, "Intracellular production of a soluble and functional monomeric streptavidin in *Escherichia coli* and its application for affinity purification of biotinylated proteins," *Protein Expr. Purification*, 46(2):268-273, 2006.

* cited by examiner

*Primary Examiner* — Christina Bradley
(74) *Attorney, Agent, or Firm* — Parker Highlander PLLC

(57) ABSTRACT

The present invention relates to a new streptavidin muteins. This mutein is The muteins are capable of oligomerization to form tetramers, with relatively strong subunit interactions, dissociation constant ($K_D$) for biotin in this mutein in the range of $10^{-7}$ to $10^{-8}$M, off-rate ($k_{off}$) for the bound biotin in the streptavidin-biotin complex in the range of $10^{-4}$ sec$^{-1}$, stable enough to allow reuse, and producible producable with reasonable production yield via secretion in a soluble functional state without the requirement of refolding streptavidin via the tedious and expensive denaturation and renaturation processes.

25 Claims, 8 Drawing Sheets

SEQUENCE LISTING

```
<160> NUMBER OF SEQ ID NOS: 19

<210> SEQ ID NO 1
<211> LENGTH: 159
<212> TYPE: PRT
<213> ORGANISM: Bacillus subtilis

<400> SEQUENCE: 1
```

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

```
Thr Phe Thr Lys Val Lys Pro Ser Ala Ala Ser Ile Asp Ala Ala Lys
    130                 135                 140

Lys Ala Gly Val Asn Gly Asn Pro Leu Asp Ala Val Gln Gln
145                 150                 155
```

<210> SEQ ID NO 2
<211> LENGTH: 477
<212> TYPE: DNA
<213> ORGANISM: Bacillus subtilis

<400> SEQUENCE: 2

```
gacccgagca aagattctaa agcacaagta tctgctgcag aagcaggaat tacaggcaca      60
tggtataatc agctgggatc tacatttatt gttacagccg gcgcagatgg agctcttaca    120
ggaacatatg aatctgctgt tggaaatgca gaatctagat acgtgcttac aggaagatat    180
gattctgcac ctgcaacaga tggatccgga acagcacttg gatggacagt tgcatggaaa    240
aacaattata gaaacgcaca tagcgctaca acatggtctg gccaatatgt gggaggtgca    300
gaagcaagaa ttaacacaca atggctttta acatctggaa caacagaagc aaatgcatgg    360
aaaagtactc ttgttggaca tgatacattt acaaaagtta aacctagcgc agcatctatc    420
gatgcagcga aaaagcagg agttaacaat ggcaatcctt tagatgcagt tcaacaa        477
```

<210> SEQ ID NO 3
<211> LENGTH: 188
<212> TYPE: PRT
<213> ORGANISM: Bacillus subtilis

<400> SEQUENCE: 3

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Asp Pro Ser
            20                  25                  30

Lys Asp Ser Lys Ala Gln Val Ser Ala Glu Ala Gly Ile Thr Gly
        35                  40                  45

Thr Trp Tyr Asn Gln Leu Gly Ser Thr Phe Ile Val Thr Ala Gly Ala
    50                  55                  60

Asp Gly Ala Leu Thr Gly Thr Tyr Glu Ser Ala Val Gly Asn Ala Glu
65                  70                  75                  80

Ser Arg Tyr Val Leu Thr Gly Arg Tyr Asp Ser Ala Pro Ala Thr Asp
                85                  90                  95

Gly Ser Gly Thr Ala Leu Gly Trp Thr Val Ala Trp Lys Asn Asn Tyr
            100                 105                 110

Arg Asn Ala His Ser Ala Thr Thr Trp Ser Gly Gln Tyr Val Gly Gly
        115                 120                 125

Ala Glu Ala Arg Ile Asn Thr Gln Trp Leu Leu Thr Ser Gly Asp Ser
    130                 135                 140

Ser Asn Gly Ser Asp Gly Ser Thr Leu Val Gly His Asp Thr Phe Thr
145                 150                 155                 160

Lys Val Lys Pro Ser Ala Ala Ser Ile Asp Ala Ala Lys Lys Ala Gly
                165                 170                 175

Val Asn Asn Gly Asn Pro Leu Asp Ala Val Gln Gln
            180                 185
```

<210> SEQ ID NO 4
<211> LENGTH: 564
<212> TYPE: DNA

<213> ORGANISM: Bacillus subtilis

<400> SEQUENCE: 4

```
atgaatatca aaaaattcgc taagcaagct acagtcctta catttacaac agcgctgctt    60
gccgggggcg ccacccaggc ctttgctgac ccgagcaaag attctaaagc acaagtatct   120
gctgcagaag cgggcattac gggcacgtgg tataatcagc tgggcagcac gtttattgtt   180
acggccggcg cagatggagc tctgacgggc acgtatgaaa gcgcggttgg caatgcagaa   240
tctagatacg ttcttacagg aagatatgat tctgcacctg caacagatgg atccggcacg   300
gcactgggct ggacagttgc atggaaaaac aattatcgca acgcacatag cgccacgacg   360
tggtctggcc aatatgttgg cggtgcagaa gcacgcatta acacacagtg gcttctgacg   420
tccggagata gcagcaatgg cagcgatggc agtactcttg ttggacatga tacatttaca   480
aaagttaaac ctagcgcagc atctatcgat gcagcgaaaa agcaggagta taacaatggc   540
aatcctttag atgcagttca acaa                                          564
```

<210> SEQ ID NO 5
<211> LENGTH: 159
<212> TYPE: PRT
<213> ORGANISM: Bacillus subtilis

<400> SEQUENCE: 5

```
Asp Pro Ser Lys Asp Ser Lys Ala Gln Val Ser Ala Ala Glu Ala Gly
  1               5                  10                  15
Ile Thr Gly Thr Trp Tyr Asn Gln Leu Gly Ser Thr Phe Ile Val Thr
             20                  25                  30
Ala Gly Ala Asp Gly Ala Leu Thr Gly Thr Tyr Glu Ser Ala Val Gly
         35                  40                  45
Asn Ala Glu Ser Arg Tyr Val Leu Thr Gly Arg Tyr Asp Ser Ala Pro
     50                  55                  60
Ala Thr Asp Gly Ser Gly Thr Ala Leu Gly Trp Thr Val Ala Trp Lys
 65                  70                  75                  80
Asn Asn Tyr Arg Asn Ala His Ser Ala Thr Thr Trp Ser Gly Gln Tyr
                 85                  90                  95
Val Gly Gly Ala Glu Ala Arg Ile Asn Thr Gln Trp Leu Leu Thr Ser
            100                 105                 110
Gly Asp Ser Ser Asn Gly Ser Asp Gly Ser Thr Leu Val Gly His Asp
        115                 120                 125
Thr Phe Thr Lys Val Lys Pro Ser Ala Ala Ser Ile Asp Ala Ala Lys
    130                 135                 140
Lys Ala Gly Val Asn Asn Gly Asn Pro Leu Asp Ala Val Gln Gln
145                 150                 155
```

<210> SEQ ID NO 6
<211> LENGTH: 477
<212> TYPE: DNA
<213> ORGANISM: Bacillus subtilis

<400> SEQUENCE: 6

```
gacccgagca agattctaa agcacaagta tctgctgcag aagcgggcat tacgggcacg    60
tggtataatc agctgggcag cacgtttatt gttacggccg gcgcagatgg agctctgacg   120
ggcacgtatg aaagcgcggt tggcaatgca gaatctagat acgttcttac aggaagatat   180
gattctgcac ctgcaacaga tggatccggc acggcactgg gctggacagt tgcatggaaa   240
aacaattatc gcaacgcaca tagcgccacg acgtggtctg gccaatatgt tggcggtgca   300
```

```
gaagcacgca ttaacacaca gtggcttctg acgtccggag atagcagcaa tggcagcgat      360
ggcagtactc ttgttggaca tgatacattt acaaaagtta aacctagcgc agcatctatc      420
gatgcagcga aaaagcagg agttaacaat ggcaatcctt tagatgcagt tcaacaa         477
```

<210> SEQ ID NO 7
<211> LENGTH: 127
<212> TYPE: PRT
<213> ORGANISM: Bacillus subtilis

<400> SEQUENCE: 7

```
Ala Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Asp Ser Ser Asn Gly Ser Asp Gly Ser Thr Leu
            100                 105                 110

Val Gly His Asp Thr Phe Thr Lys Val Lys Pro Ser Ala Ala Ser
        115                 120                 125
```

<210> SEQ ID NO 8
<211> LENGTH: 381
<212> TYPE: DNA
<213> ORGANISM: Bacillus subtilis

<400> SEQUENCE: 8

```
gcagaagcgg gcattacggg cacgtggtat aatcagctgg gcagcacgtt tattgttacg      60
gccggcgcag atggagctct gacgggcacg tatgaaagcg cggttggcaa tgcagaatct     120
agatacgttc ttacaggaag atatgattct gcacctgcaa cagatggatc cggcacggca     180
ctgggctgga cagttgcatg gaaaaacaat tatcgcaacg cacatagcgc cacgacgtgg     240
tctggccaat atgttggcgg tgcagaagca cgcattaaca cacagtggct tctgacgtcc     300
ggagatagca gcaatggcag cgatggcagt actcttgttg gacatgatac atttacaaaa     360
gttaaaccta gcgcagcatc t                                               381
```

<210> SEQ ID NO 9
<211> LENGTH: 188
<212> TYPE: PRT
<213> ORGANISM: Bacillus subtilis

<400> SEQUENCE: 9

```
Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala Asp Pro Ser
            20                  25                  30

Lys Asp Ser Lys Ala Gln Val Ser Ala Ala Glu Ala Gly Ile Thr Gly
        35                  40                  45

Thr Trp Tyr Asn Gln Leu Gly Ser Thr Phe Ile Val Thr Ala Gly Ala
```

```
        50                  55                  60
Asp Gly Ala Leu Thr Gly Thr Tyr Glu Ser Ala Val Gly Asn Ala Glu
 65                  70                  75                  80

Ser Arg Tyr Val Leu Thr Gly Arg Tyr Asp Ser Ala Pro Ala Thr Asp
                 85                  90                  95

Gly Ser Gly Thr Ala Leu Gly Trp Thr Val Ala Trp Lys Asn Asn Tyr
            100                 105                 110

Arg Asn Ala His Ser Ala Thr Thr Trp Ser Gln Tyr Val Gly Gly
        115                 120                 125

Ala Glu Ala Arg Ile Asn Thr Gln Trp Leu Leu Thr Ser Gly Asp Ser
    130                 135                 140

Ser Asn Gly Ser Asp Gly Ser Thr Leu Val Gly Cys Asp Thr Phe Thr
145                 150                 155                 160

Lys Val Lys Pro Ser Ala Ala Ser Ile Asp Ala Ala Lys Lys Ala Gly
                165                 170                 175

Val Asn Asn Gly Asn Pro Leu Asp Ala Val Gln Gln
            180                 185

<210> SEQ ID NO 10
<211> LENGTH: 579
<212> TYPE: DNA
<213> ORGANISM: Bacillus subtilis

<400> SEQUENCE: 10
atgaatatca aaaaattcgc taagcaagct acagtcctta catttacaac agcgctgctt      60
gccgggggcg ccacccaggc ctttgctgac ccgagcaaag attctaaagc acaagtatct     120
gctgcagaag cgggcattac gggcacgtgg tataatcagc tgggcagcac gtttattgtt     180
acggccggcg cagatggagc tctgacgggc acgtatgaaa gcgcggttgg caatgcagaa     240
tctagatacg ttcttacagg aagatatgat tctgcacctg caacagatgg atccggcacg     300
gcactgggct ggacagttgc atggaaaaac aattatcgca acgcacatag cgccacgacg     360
tggtctggcc aatatgttgg cggtgcagaa gcacgcatta acacacagtg gcttctgacg     420
tccggagata gcagcaatgg cagcgatggc agtactcttg ttggatgcga tacatttaca     480
aaagttaaac ctagcgcagc atctatcgat gcagcgaaaa agcaggagt taacaatggc      540 aatcctttag atgcagttca acaataatga tcagatatc                            579

<210> SEQ ID NO 11
<211> LENGTH: 8
<212> TYPE: PRT
<213> ORGANISM: Bacillus subtilis

<400> SEQUENCE: 11

Asp Ser Ser Asn Gly Ser Asp Gly
 1               5

<210> SEQ ID NO 12
<211> LENGTH: 16
<212> TYPE: PRT
<213> ORGANISM: Bacillus subtilis

<400> SEQUENCE: 12

Leu Thr Ser Gly Thr Thr Glu Ala Asn Ala Trp Lys Ser Thr Leu Val
 1               5                  10                  15

<210> SEQ ID NO 13
<211> LENGTH: 7
```

```
<212> TYPE: PRT
<213> ORGANISM: Bacillus subtilis

<400> SEQUENCE: 13

Thr Thr Glu Ala Asn Ala Lys
1               5

<210> SEQ ID NO 14
<211> LENGTH: 8
<212> TYPE: PRT
<213> ORGANISM: Bacillus subtilis

<400> SEQUENCE: 14

Asp Ser Ser Asn Gly Ser Asp Gly
1               5

<210> SEQ ID NO 15
<211> LENGTH: 8
<212> TYPE: PRT
<213> ORGANISM: Bacillus subtilis

<400> SEQUENCE: 15

Asp Ser Ser Asn Gly Ser Asp Gly
1               5

<210> SEQ ID NO 16
<211> LENGTH: 6
<212> TYPE: PRT
<213> ORGANISM: Bacillus subtilis

<400> SEQUENCE: 16

Asp Ser Asn Gly Ser Gly
1               5

<210> SEQ ID NO 17
<211> LENGTH: 4
<212> TYPE: PRT
<213> ORGANISM: Bacillus subtilis

<400> SEQUENCE: 17

Asp Asn Gly Gly
1

<210> SEQ ID NO 18
<211> LENGTH: 2
<212> TYPE: PRT
<213> ORGANISM: Bacillus subtilis

<400> SEQUENCE: 18

Asn Gly
1

<210> SEQ ID NO 19
<211> LENGTH: 118
<212> TYPE: PRT
<213> ORGANISM: Bacillus subtilis

<400> SEQUENCE: 19

Gly Ile Thr Gly Thr Trp Tyr Asn Gln Leu Gly Ser Thr Phe Ile Val
1               5                   10                  15

Thr Ala Gly Ala Asp Gly Ala Leu Thr Gly Thr Tyr Glu Ser Ala Val
            20                  25                  30

Gly Asn Ala Glu Ser Arg Tyr Val Leu Thr Gly Arg Tyr Asp Ser Ala
        35                  40                  45
```

```
Pro Ala Thr Asp Gly Ser Gly Thr Ala Leu Gly Trp Thr Val Ala Trp
    50              55                  60

Lys Asn Asn Tyr Arg Asn Ala His Ser Ala Thr Thr Trp Ser Gly Gln
65              70                  75                      80

Tyr Val Gly Gly Ala Glu Ala Arg Ile Asn Thr Gln Trp Leu Leu Thr
                85                  90                  95

Ser Gly Thr Thr Glu Ala Asn Ala Trp Lys Ser Thr Leu Val Gly His
            100             105             110

Asp Thr Phe Thr Lys Val
            115
```

TETRAMERIC STREPTAVIDIN MUTEIN WITH REVERSIBLE BIOTIN BINDING CAPABILITY

The present application claims benefit of priority to U.S. Provisional Application Ser. No. 61/514,325, filed Aug. 2, 2011, the entire contents of which are hereby incorporated by reference.

BACKGROUND OF THE INVENTION

1. Field of the Invention

The present invention relates to fields of protein biology and diagnostics. More particularly, the present invention relates to improved muteins of streptavidin that specifically yet reversibly bind biotin.

2. Description of Related Art

Wild-type streptavidin is a tetrameric protein with four identical subunits. Two dimers self-associate to form a tetrameric structure. Each subunit can bind one biotin tightly with a dissociation constant ($K_D$) in the range of $10^{-13}$ to $10^{-14}$ M (Wilchek and Bayer, 1990). This binding is considered to be irreversible and streptavidin has been applied to capture and immobilize biotinylated biomolecules. It is widely used in development of many diagnostic kits, biosensor chip, protein and DNA arrays and Western blot studies. However, wild-type streptavidin is not suitable for purification of biotinylated biomolecules. To extend its application, it would be ideal to develop engineered streptavidin muteins with reversible biotin binding ability so that these muteins can be applied to purify biotinylated molecules, to study protein-protein interactions (with one of the interacting proteins to be biotinylated) and to develop reusable biosensor chips and bioreactors (e.g., traditional bioreactors will have enzymes chemically immobilized. After many rounds of usage, bioreactors with the immobilized enzymes will become useless when the immobilized enzymes lose their activities. With the engineered streptavidin that can bind biotin in a reversible manner, one can immobilize these engineered streptavidin proteins to the bioreactor. The enzymes of interest can then be biotinylated and loaded to bioreactors with the immobilized streptavidin muteins to generate functional bioreactors. When the enzymes lose their activity, these inactive enzymes can be eluted off by biotin and the bioreactor can be reloaded with a new batch of biotinylated enzymes).

To develop streptavidin muteins with reversible binding ability, two approaches are common. The first approach is to replace one or more streptavidin amino acid residues that are critical in biotin binding with different residues. These changes can result in lowering the biotin binding affinity in these muteins (Qureshi et al., 2001; U.S. Pat. No. 6,312,916 B1). The second approach is to develop recombinant monomeric streptavidin (Wu and Wong, 2005a). This is based on the fact that a streptavidin subunit does not have a complete biotin binding pocket. A biotin binding pocket in subunit A requires a tryptophan 120 (Trp-120) residue from subunit D. This Trp-120 has been demonstrated to play an important role in biotin binding (Chilkoti et al., 1995).

A change of this residue to alanine (W120A) results in a streptavidin mutein (W120A) with a $K_d$ of $3 \times 10^{-9}$M for biotin (U.S. Pat. No. 6,312,916 B1). Furthermore, affinity matrices of monomeric avidin have been developed. The dissociation constant of biotin for monomeric avidin is reported to be ~$10^{-7}$M (Kohanski and Lane, 1990). The inventors reported the successful generation of engineered monomeric streptavidin (Wu and Wong, 2005a) via the recombinant DNA method. This monomeric streptavidin also has the biotin binding affinity (expressed in terms of the dissociation constant, $K_d$) in the range of $10^{-7}$M. However, each of the above-mentioned approaches has certain limitations, and thus improved muteins of streptavidin are needed.

SUMMARY OF THE INVENTION

Thus, in accordance with the present invention, there is provided a streptavidin mutein comprising the sequence Asp-Ser-Ser-Asn-Gly-Ser-Asp-Gly (SEQ ID NO:11) at positions 114-121 corresponding to full-length wild-type streptavidin (SEQ ID NO:1). The mutein may further comprise $Cys_{127}$. The mutein may comprise 127 residues, 159 residues, 188 residues, may comprise SEQ ID NO:3, SEQ ID NO:5 or SEQ ID NO:7, may consist of SEQ ID NO:3, SEQ ID NO:5 or SEQ ID NO:7, and may further comprise $Cys_{127}$ in conjunction with each of the foregoing. In particular, the mutein may comprise SEQ ID NO: 9.

In another embodiment, there is provided a nucleic acid encoding there is provided a streptavidin mutein comprising the sequence Asp-Ser-Ser-Asn-Gly-Ser-Asp-Gly (SEQ ID NO:11) at positions 114-121 corresponding to full-length wild-type streptavidin (SEQ ID NO:1). The nucleic acid may encode a mutein may further comprising $Cys_{127}$. The nucleic acid may encode a mutein may comprise 127 residues, 159 residues, 188 residues, may comprise SEQ ID NO:3, SEQ ID NO:5 or SEQ ID NO:7, may consist of SEQ ID NO:3, SEQ ID NO:5 or SEQ ID NO:7, and may further comprise $Cys_{127}$ in conjunction with each of the foregoing. In particular, The nucleic acid may encode a mutein comprising SEQ ID NO: 9.

Also provided is a tetrameric streptavidin mutein complex comprising four streptavidin mutein subuntis comprising the sequence Asp-Ser-Ser-Asn-Gly-Ser-Asp-Gly (SEQ ID NO:11) at positions 114-121 corresponding to full-length wild-type streptavidin (SEQ ID NO:1). The complex may further comprise a bound biotin molecule. The complex may further comprise two bound biotin molecules. The complex may further comprise three bound biotin molecules. The complex may further comprise four bound biotin molecules.

Yet another embodiment comprises a method of binding a biotin molecule comprising contacting a biotin molecule with a tetrameric streptavidin mutein complex comprising four streptavidin mutein subuntis comprising the sequence Asp-Ser-Ser-Asn-Gly-Ser-Asp-Gly (SEQ ID NO:11) at positions 114-121 corresponding to full-length wild-type streptavidin (SEQ ID NO:1). The biotin molecule may be bound to a matrix, such as a porous or nonporous particle, a membrane, a monolithic support, or a natural or synthetic polymer, or bound to a free molecule, such as a protein, a glycoprotein, a peptide, an oligonucleotide, a polynucleotide, a carbohydrate, a lipid, a glycolipid, an organic chemical, a synthetic polymer, an organo-metal chelate, a fluorescent molecule, a microparticle, a nanoparticles, or a drug, or a combination of any of the foregoing. The method may further comprise the step of reversing the binding of the biotin molecule and the complex.

A further embodiment comprises a method of purifying a target molecule comprising (a) providing a streptavidin mutein complex comprising two to four streptavidin mutein subuntis comprising the sequence Asp-Ser-Ser-Asn-Gly-Ser-Asp-Gly (SEQ ID NO:11) at positions 114-121 corresponding to full-length wild-type streptavidin (SEQ ID NO:1), wherein aid streptavidin mutein complex is immobilized to a matrix; (b) contacting a target molecule/biotin molecule complex with the streptavidin mutein complex on the matrix; and (c) washing the matrix to remove non-specifically bound material. The method may further comprise (d) eluating bound target molecule/biotinylated molecule complex from the matrix. The target molecule may be a protein, a glycoprotein, a peptide, an oligonucleotide, a polynucleotide, a carbohydrate, a lipid, a glycolipid, an organic chemical, a synthetic polymer, an organo-metal chelate, a fluorescent molecule, a microparticle, a nanoparticles, or a drug, or a combination of any of the foregoing. The matrix may be a porous or nonporous particle, a membrane, a monolithic support, or a natural or synthetic polymer.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
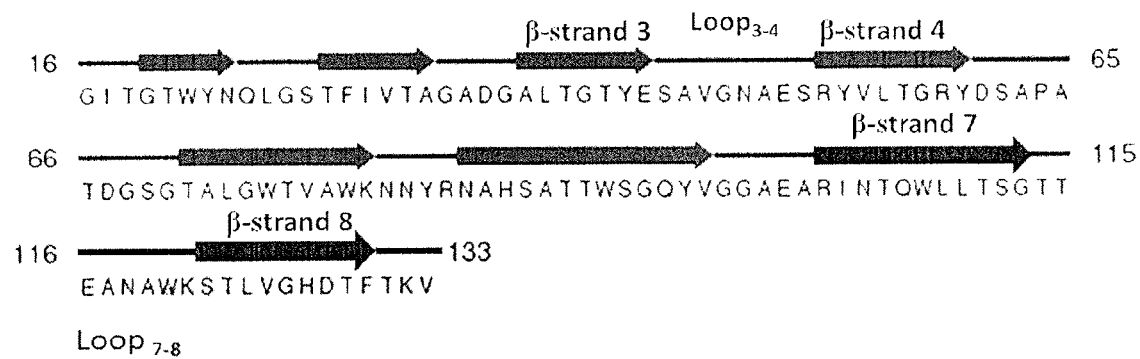
FIG. 1. Secondary structure of streptavidin (SEQ ID NO: 19). Streptavidin is mainly composed of 8 β-strands (blue arrows). The numbering of the amino acids in this figure is based on the structure of the streptavidin subunit determined by X-ray crystallographic study. Locations of loop$_{3-4}$ and loop$_{7-8}$ are indicated. W120 is located in loop$_{7-8}$. This loop is also named as the Trp-120 loop.

In studies described below, the inventors took a new approach to design and develop an improved, engineered streptavidin with reversible biotin binding capability, along with other desirable features. With the objective to develop an engineered streptavidin with reversible biotin binding capability, an idealized streptavidin mutein should have the following desirable properties. First, it should be dimeric or tetrameric in nature so that there are two biotin binding sites per dimer or four biotin binding sites per tetramer. In reference to the monomeric streptavidin, streptavidin in either the dimeric or tetrameric state will have less hydrophobic interface exposed to the surface so that non-specific hydrophobic interactions between engineered streptavidin and proteins in the crude sample can be minimized. Second, the strength of the subunit interaction should be relatively strong. When one subunit of a dimeric or tetrameric engineered streptavidin is immobilized, the other three subunits can stably associate with this covalently immobilized subunit so that no streptavidin subunit will be stripped off from the column during the wash and elution steps. Third, the dissociation constant ($K_D$) for biotin in this mutein should be in the range of $10^{-7}$ to $10^{-8}$M. Fourth, the off-rate ($k_{off}$) for the bound biotin in the streptavidin-biotin complex is ideally in the range of $10^{-4}$ sec$^1$. Therefore, the estimated half-life ($t_{1/2}=0.693/k_{off}$) of the bound biotin will then be in the range of 10-30 min. With the combination of conditions three and four, the interaction would be both strong and specific to allow non-specific molecules to be washed off from the matrix without leakage of the bound biotinylated molecules during the wash step. At the same time, it will allow the biotinylated molecules to be eluted off from the column efficiently with a good recovery. A fine balance between good affinity towards biotinylated molecules and good recovery is essential for this idealized streptavidin. Fifth, the engineered streptavidin muteins immobilized to the matrix should be stable enough to allow reuses of the matrix for purification of biotinylated molecules. Sixth, the engineered streptavidin can be produced with reasonable production yield in a soluble functional state without the requirement of refolding streptavidin via the tedious and expensive denaturation and renaturation processes. The use of *Bacillus subtilis* WB800, an 8 protease deficient strain, for secretory production of streptavidin is an attractive approach (Wu et al., 2002).

1. Streptavidin and Biotin

A. Steptavidin

Streptavidin is a 52,800 dalton tetrameric protein purified from the bacterium *Streptomyces avidinii*. It has an extraordinarily high affinity for biotin (also known as vitamin B7); the dissociation constant ($K_d$) of the biotin-streptavidin complex is on the order of $\approx 10^{-14}$ mol/L, making it one of the strongest non-covalent interactions known in nature. Streptavidin is used extensively in molecular biology and bionanotechnology due to the streptavidin-biotin complex's resistance to organic solvents, denaturants (e.g., guanidinium chloride), detergents (e.g., SDS, Triton), proteolytic enzymes, and extremes of temperature and pH. The sequence for wild-type streptavidin is provided in SEQ ID NO:1.

The crystal structure of streptavidin with biotin bound was first solved in 1989. The N and C termini of the 159 residue full-length protein are processed to give a shorter 'core' streptavidin, usually composed of residues 13-139; removal of the N and C termini is not necessary for the high biotin-binding affinity. The secondary structure of a streptavidin monomer is composed of eight antiparallel β-strands, which fold to give an antiparallel beta-barrel tertiary structure. A biotin binding-site is located at one end of each β-barrel. Four identical streptavidin monomers (i.e., four identical β-barrels) associate to give streptavidin's tetrameric quaternary structure. The biotin binding-site in each barrel consists of residues from the interior of the barrel, together with a conserved Trp120 from neighbouring subunit. In this way, each subunit contributes to the binding site on the neighbouring subunit, and so the tetramer can also be considered a dimer of functional dimers.

The numerous crystal structures of the streptavidin-biotin complex have shed light on the origins of the remarkable affinity. Firstly, there is high shape complementarity between the binding pocket and biotin. Secondly, there is an extensive network of hydrogen bonds formed to biotin when in the binding site. There are eight hydrogen bonds directly made to residues in the binding site (the so called 'first shell' of hydrogen bonding), involving residues Asn23, Tyr43, Ser27, Ser45, Asn49, Ser88, Thr90 and Asp128. There is also a 'second shell' of hydrogen bonding involving residues that interact with the first shell residues. However, the streptavidin-biotin affinity exceeds that which would be predicted from the hydrogen bonding interactions alone, alluding to another mechanism contributing to the high affinity. The biotin-binding pocket is hydrophobic, and there are numerous van der Waals contacts and hydrophobic interactions made to the biotin when in the pocket, which is also thought to account for the high affinity. In particular, the pocket is lined with conserved tryptophan residues. Lastly, biotin binding is accompanied by the stabilisation of a flexible loop connecting β strands 3 and 4 (L3/4), which closes over the bound biotin, acting like a 'lid' over the binding pocket and contributing to the extremely slow biotin dissociation rate.

Most attempts at mutating streptavidin result in a lowered biotin-binding affinity, which is to be expected in such a highly optimised system. However, a recently engineered mutant of streptavidin, named traptavidin, was found to have more than ten-fold slower biotin dissociation, in addition to higher thermal and mechanical stability. This decreased dissociation rate was accompanied by a two-fold decrease in the association rate.

Among the most common uses are the purification or detection of various biomolecules. The strong streptavidin-biotin bond can be used to attach various biomolecules to one another or onto a solid support. A further application is the so called Strep-tag, which is an optimized system for the purification and detection of proteins. Streptavidin is widely used in Western blotting and immunoassays conjugated to some reporter molecule, such as horseradish peroxidase.

Streptavidin is a tetramer and each subunit binds biotin with equal affinity. Multivalency is an advantage in some applications, for example where avidity effects improve the ability of molecules attached to streptavidin to detect specific T cells. In other cases, such as the use of streptavidin for imaging specific proteins on cells, multivalency can perturb the function of the protein of interest. Monovalent streptavidin is an engineered recombinant form of streptavidin which is a tetramer but only one of the four binding sites is functional. This single binding site has $10^{-14}$ mol/L affinity and cannot cause cross-linking. In contrast, monomeric streptavidin is a recombinant form of streptavidin with mutations to break the tetramer into a monomer and to enhance the solubility of the resultant isolated subunit. Monomeric streptavidin has an affinity for biotin of $10^{-7}$ mol/L and so is not ideal for labeling applications but is useful for purification, where reversibility is desirable.

Streptavidin is not the only protein capable of binding to biotin with high affinity. Avidin is the other most notable biotin-binding protein, which is evolutionarily unrelated to streptavidin but has very similar properties. Originally isolated from egg white, avidin only has 30% sequence identity to streptavidin, but almost identical secondary, tertiary and quaternary structure. It has a higher affinity for biotin ($K_d \sim 10^{-15}$M) but in contrast to streptavidin, it is glycosylated, positively charged, has pseudo-catalytic activity (it can enhance the alkaline hydrolysis of an ester linkage between biotin and a nitrophenyl group) and has a higher tendency for aggregation. Also, streptavidin is the better biotin-conjugate binder; avidin has a lower binding affinity than streptavidin when biotin is conjugated to another molecule, despite avidin having the higher affinity for free, unconjugated biotin.

Streptavidin has a mildly acidic isoelectric point (pI) of ~5, but a recombinant form of streptavidin with a near-neutral pI is also commercially available Because streptavidin lacks any carbohydrate modification and has a near-neutral pI, it has the advantage of much lower nonspecific binding than avidin. Deglycosylated avidin (NeutrAvidin) is more comparable to the size, pI and nonspecific binding of streptavidin.

B. Biotin

As discussed above, biotin is a water-soluble B-complex vitamin (vitamin B7) It was discovered by Bateman in 1916. It is composed of a ureido (tetrahydroimidizalone) ring fused with a tetrahydrothiophene ring. A valeric acid substituent is attached to one of the carbon atoms of the tetrahydrothiophene ring. Biotin is a coenzyme in the metabolism of fatty acids and leucine, and it plays a role in gluconeogenesis.

Biotin is necessary for cell growth, the production of fatty acids, and the metabolism of fats and amino acids. It plays a role in the citric acid cycle, which is the process by which biochemical energy is generated during aerobic respiration. Biotin not only assists in various metabolic reactions but also helps to transfer carbon dioxide. Biotin may also be helpful in maintaining a steady blood sugar level. Biotin is often recommended for strengthening hair and nails. As a consequence, it is found in many cosmetics and health products for the hair and skin, though it cannot be absorbed through the hair or skin itself. Biotin deficiency is rare because, in general, intestinal bacteria produce biotin in excess of the body's daily requirements.

The empirical formula of biotin is $C_{10}H_{16}O_3N_2S$. Biotin has an unusual structure. It has two side rings fused together. The two side rings are imidazole and thiophene. Biotin is a heterocyclic S-containing monocarboxylic acid. Biotin D(+) is a cofactor responsible for carbon dioxide transfer in several carboxylase enzymes: Acetyl-CoA carboxylase alpha, Acetyl-CoA carboxylase beta, Methylcrotonyl-CoA carboxylase, Propionyl-CoA carboxylase and Pyruvate carboxylase. Thus, it is important in fatty acid synthesis, branched-chain amino acid catabolism, and gluconeogenesis. Biotin covalently attaches to the epsilon-amino group of specific lysine residues in these carboxylases. This biotinylation reaction requires ATP and is catalyzed by holocarboxylase synthetase. The attachment of biotin to various chemical sites can be used as an important laboratory technique to study various processes including protein localization, protein interactions, DNA transcription, and replication. Biotinidase itself is known to be able to biotinylate histone proteins, but little biotin is found naturally attached to chromatin.

Biotin binds very tightly to the tetrameric proteins avidin, streptavidin and neutravidin with a dissociation constant $K_d$ in the order of $10^{-15}$ M, which is one of the strongest known protein-ligand interactions, approaching the covalent bond in strength. This is often used in different biotechnological applications. Until 2005, very harsh conditions were required to break the biotin-streptavidin bond.

Biotin is consumed from a wide range of food sources in the diet, however there are few particularly rich sources. Foods with a relatively high biotin content include raw egg yolk (however, the consumption of egg whites with egg yolks minimizes the effectiveness of egg yolk's biotin in one's body), liver, some vegetables and peanuts. The dietary biotin intake in Western populations has been estimated to be 35 to 70 µg/d (143-287 nmol/d). Biotin is also available from supplements. The synthetic process developed by Sternbach and Goldberg in the 1940's uses fumaric acid as a starting material and is identical to the natural product.

Studies on the bioavailability of biotin have been conducted in rats and in chicks. From these studies, it was concluded that biotin bioavailability may be low or variable, depending on the type of food being consumed. In general, biotin exists in food as protein bound form or biocytin. Proteolysis by protease is required prior to absorption. This process assists free biotin release from biocytin and protein-bound biotin. The biotin present in corn is readily available; however, most grains have about a 20-40% bioavailability of biotin.

A possible explanation for the wide variability in biotin bioavailability is that it is due to ability of an organism to break various biotin-protein bonds from food. Whether an organism has an enzyme with the ability to break that bond will determine the bioavailability of biotin from the foodstuff.

As mentioned above, biotin is used experimentall by chemically linking it to proteins for biochemical assays. Its small size means the biological activity of the protein will most likely be unaffected. This process is called biotinylation. Because both streptavidin and avidin bind biotin with high affinity ($K_d$ of ~$10^{-14}$ mol/L) and specificity, biotinylated proteins of interest can be isolated from a sample by exploiting this highly-stable interaction. The sample is incubated with streptavidin/avidin beads, allowing capture of the biotinylated protein of interest. Any other proteins binding to the biotinylated molecule will also stay with the bead and all other unbound proteins can be washed away. However, due to the extremely strong streptavidin-biotin interaction, very harsh conditions are needed to elute the biotinylated protein from the beads (typically 6M GuHCl at pH 1.5), which often will denature the protein of interest. To circumvent this problem, beads conjugated to monomeric avidin can be used, which has a decreased biotin-binding affinity of ~$10^{-8}$ mol/L, allowing the biotinylated protein of interest to be eluted with excess free biotin. ELISAs often make use of biotinylated primary antibodies against the antigen of interest, followed by a detection step using streptavidin conjugated to a reporter molecule, such as horseradish peroxidase.

C. Steptavidin Muteins

Figure 2:
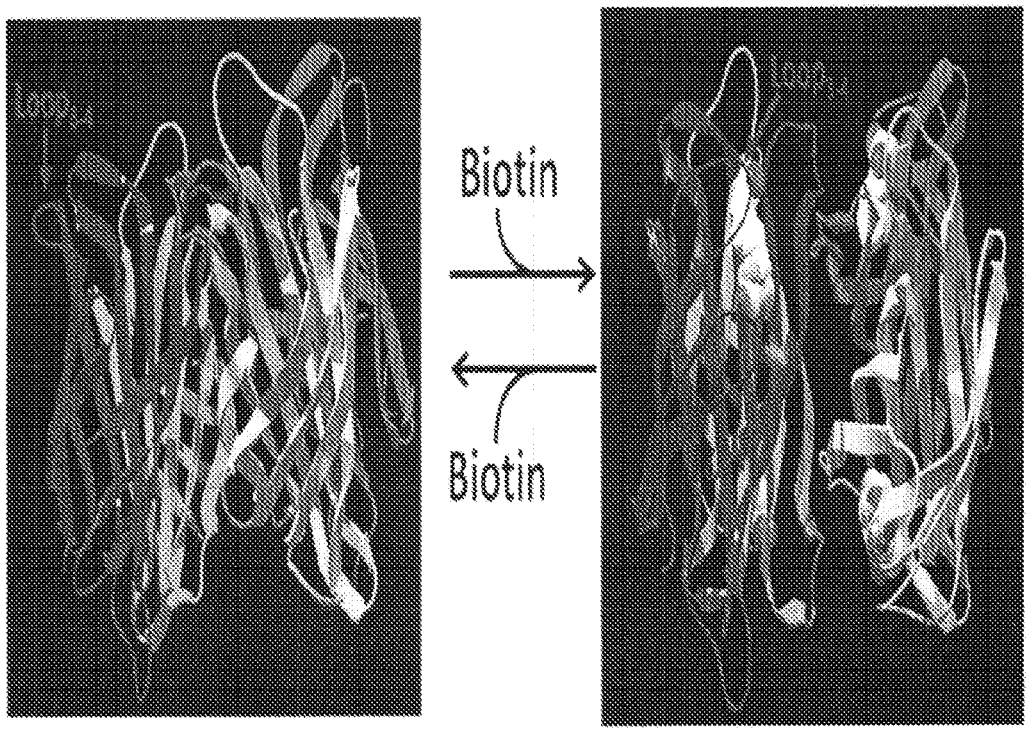
FIG. 2. Biotin binding and exit paths in wild-type streptavidin. Loop$_{3-4}$ is in the open conformation as shown in the left panel to allow biotin binding. Loop$_{3-4}$ is in the closed position as shown in the right panel.

To understand the approach taken by the present inventors, one has to recognize two important loops (loop$_{3-4}$ and loop$_{7-8}$) present in the wild-type streptavidin. These loops are shown in FIG. 1. In wild-type streptavidin, loop$_{3-4}$ has been shown to be flexible in the absence of biotin and will mainly be in the open position. In contrast, after the binding of biotin to streptavidin, loop$_{3-4}$ becomes immobilized and is in the closed position (Freitag et al., 1997). Therefore, in the current model, loop$_{3-4}$ is suggested to function as a gateway for both the entry and exit of biotin into the biotin binding pockets in streptavidin (FIG. 2).

Figure 3:
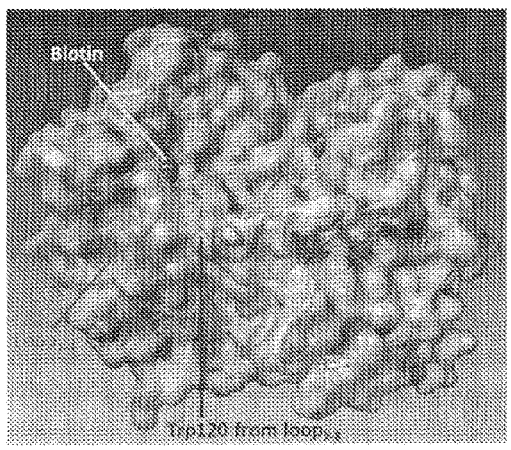
FIG. 3. Two different views of the trapped biotin in the biotin binding pocket of subunit A in the wild-type streptavidin. Left panel: Loop$_{3-4}$ from subunit A (red) and loop$_{7-8}$ from subunit D (blue) form part of the walls in the biotin binding pocket in subunit A. Trp-120 is a key residue located in loop$_{7-8}$. This residue interacts strongly with biotin. Right panel: Biotin is clearly trapped in the biotin binding pocket. Without opening of the lid formed by loop$_{3-4}$, biotin cannot escape from the biotin binding pocket. Even this biotin does not have any interaction with residues in the biotin binding pocket, it is still physically trapped in the biotin binding pocket and can be recaptured easily.
Figure 3:
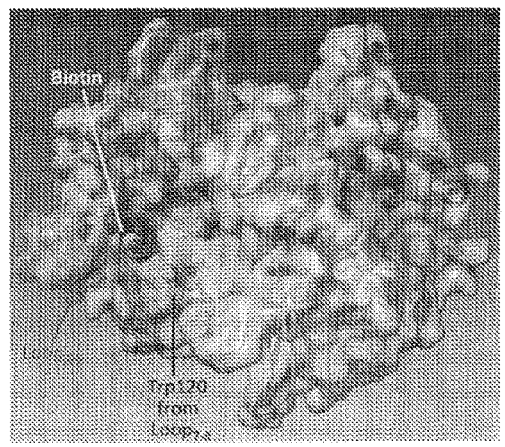

Since most of the residues in loop$_{3-4}$ (e.g., S45, V47, G48, N49 and A50) interact strongly with biotin, this loop will mainly remain in the closed state in the presence of biotin. Biotin also interacts strongly with residues in the biotin binding pocket (e.g., Tyr-43, Ser-88, Thr-90, Trp-79, Trp-92, Trp-108 and Trp-120) via both hydrogen bonding and hydrophobic interactions. At the same time, it is physically trapped in the biotin binding site as shown in FIG. 3.

In this study, an attempt was made to create a back door formed by loop$_{7-8}$ in streptavidin to allow the trapped biotin to escape from the biotin binding pocket even the first door (loop$_{3-4}$) is still in the closed configuration. This objective can be achieved by two approaches. The first one is to create a flexible loop$_{7-8}$ with all the amino acids naturally present in loop$_{7-8}$ replaced by other amino acids. This engineered loop retains the same loop length as observed in the original loop$_{7-8}$ of the wild-type streptavidin (i.e., with a total of 8 amino acids in this engineered loop). In the design of this loop, asparagine and glycine were introduced at the center of the loop since they are known to introduce a turn in the loop structure. Both the DSS (aspartate, serine and serine) and SDG (serine, aspartate and glycine) sequences were introduced to form the left and right arms of the loop, respectively (Table 1). These amino acids were selected because they have a high propensity for intrinsic disorder. Since a glycine (highlighted in light blue in Table 1) is naturally present at the left border of the sequence flanking loop$_{7-8}$, a glycine is introduced to the right end of the loop. These two glycine residues can potentially function as hinge points to induce flexibility to the engineered loop. Two aspartic acid residues are in this loop to adjust the isoelectric point of the engineered 8-aa-loop mutein to 5.0. Since the natural streptavidin has the pI in the range of 5-6. This engineered mutein will have the pI comparable to the natural one. This feature is desirable since the engineered mutein will be slightly negatively charged at pH7. This will help improve solubility and will not have too many non-specific electrostatic interactions with proteins in the crude samples. Absence of Trp-120 in this engineered loop should weaken the interaction between biotin and streptavidin. X-ray crystallographic studies (Freitag et al., 1998) of W120A mutein demonstrate that loop$_{7-8}$ in this mutein is still in a rigid conformation no matter in the presence or absence of biotin. This finding illustrates that weakening the major interactions between loop$_{7-8}$ and biotin is not sufficient to allow loop$_{7-8}$ to become mobile. Replacement of other residues in loop$_{7-8}$ is needed to weaken any interactions between the loop residues and their adjacent residues in streptavidin. Introduction of amino acid residues with high propensity of disorder to loop$_{7-8}$ should further increase the chance to make this engineered loop mobile. If this design is successful, the engineered loop$_{7-8}$ should act as an unlocked mobile door swinging between the open and closed states even in the presence of biotin. However, there is no guaranty that the engineered loop will truly be mobile. Even if the engineered loop is flexible, it is still not sure whether the magnitude of the loop movement would be dramatic enough to create sufficient room for the escape of the trapped biotin.

The second approach is to shorten the length of the loop in such a way that the surface area of the wall formed by loop$_{7-8}$ in the biotin binding pocket will be reduced or even be eliminated. This will create an opening to allow the trapped biotin in the biotin binding site to escape from streptavidin. A set of engineered loops with the loop length ranged from 2 to 6 amino acids was designed (Table 1). It is expected that muteins with shorter loops will create a bigger hole in the biotin binding pocket. A trapped biotin should be able to escape easier from the biotin binding pocket in these muteins. Besides the above-mentioned 4 mutants, another loop mutant was constructed. Trp-120 in this mutein was deleted. The rest of the sequence in this loop was the same as in the wild-type streptavidin. This mutant is designated ΔW (or dW, d for deletion). In the preliminary study, the 4-amino-acid-loop mutein was selected for analysis. The protein was produced from *B. subtilis* via secretion. Purified proteins were chemically coupled to the agarose matrix. This matrix could bind biotinylated proteins. However, some streptavidin mutein proteins could be eluted off from the column during the elution step from the streptavidin mutein matrix. Since only one out of 4 subunits in the tetrameric streptavidin mutein was expected to be coupled to the matrix, this observation suggested that changes in the loop$_{7-8}$ structure might result in weakening the subunit interactions in the tetrameric streptavidin mutein. To avoid this complication, a H127C mutation (Reznik et al., 1996) was introduced to two constructs (the 8-amino-acid-loop mutein and the ΔW mutein). The resulting muteins are designated 8-aa-loop-H127C mutein and ΔW-HC mutein (HC for the H127C mutation), respectively. The H127C mutation has been reported (Reznik et al., 1996) to allow the subunit A to crosslink to subunit C via a disulfide bond. Same crosslink is expected between subunit B and subunit D. These disulfide bonds are expected to strengthen the subunit interactions. The efficiency for disulfide bond formation in streptavidin with this H127C mutation is 80-90%.

TABLE 1

| Streptavidin | Features of the Loop$_{7-8}$ Muteins Trp-120 loop (or loop$_{7-8}$) | H127C | SEQ ID NO: |
|---|---|---|---|
| Wild-type | L T S G$_{113}$ T T E A N A W K S$_{122}$ T L V | − | 12 |
| ΔW-HC (dW-H127C) | T T E A N A K | + | 13 |
| 8 aa loop H127C | D S S N G S D G | + | 14 |
| 8 aa loop | D S S N G S D G | − | 15 |
| 6 aa loop | D S N G S G | − | 16 |
| 4 aa loop | D N G G | − | 17 |
| 2 aa loop | N G | − | 18 |

The sequences flanking the Trp-120 loop (loop$_{7-8}$) are shown in bold. The amino acid sequences in the natural and engineered Trp-120 loops are underlined.

In order to characterize these muteins, it is essential to purify each of these muteins for further analyses. The muteins were shown to be able to bind to the biotin-agarose column and could be eluted off from the matrix by adding 4 mM biotin into the binding buffer. After dialysis to remove any biotin from the pooled elution fraction, the purified muteins could rebind to the biotin-agarose matrix and could be eluted off again by 4 mM biotin in the buffer. This indicates the reversible biotin binding capability in these muteins.

The kinetic parameters for these muteins were determined using the BIAcore biosensor. Biotinylated IgG proteins were immobilized to the sensor chip and purified streptavidin muteins were injected to determine the binding properties:

TABLE 2

Kinetic parameters of biotin binding in streptavidin muteins

| | ΔWHC or dWHC | 2-aa-loop mutein | 6-aa-loop mutein | 8-aa-loop H127C mutein | SAV mutein from Roche (S27R, S45R, L110W) |
|---|---|---|---|---|---|
| $k_a$ or $k_{on}$ ($M^{-1}s^{-1}$) | $4.96 \times 10^4$ | $6.3 \times 10^4$ | $2.43 \times 10^4$ | $2.21 \times 10^4$ | $4.5 \times 10^4$ |
| $k_d$ or $k_{off}$ ($s^{-1}$) | $4.0 \times 10^{-4}$ | $7.02 \times 10^{-5}$ | $7.59 \times 10^{-5}$ | $4.28 \times 10^{-4}$ | $5.9 \times 10^{-3}$ |
| $K_d$ (M) | $8.1 \times 10^{-9}$ | $1.12 \times 10^{-9}$ | $3.13 \times 10^{-9}$ | $1.9 \times 10^{-8}$ | $1.3 \times 10^{-7}$ |
| $t_{1/2}$ (min)* | 28.9 | 165 | 152 | 27 | 1.96 |

*$t_{1/2}$ is the half-life of biotin in the SAV-biotin complex. It is estimated based on the following equation: $t_{1/2}$ (min) = $0.693/k_{off}/60$. The kinetic data for the Roche SAV mutein are from reference (U.S. Pat. No. 6,312,916 B1). This mutein binds biotin in a reversible manner.

The binding affinity is commonly expressed in terms of the dissociation constant ($K_d$). ΔW-HC carrying the Trp-120 deletion has the biotin binding affinity ($K_d$=8.1×10$^{-9}$M) comparable to that ($K_d$~3×10$^{-9}$M) of the W120A mutein. This is not too unexpected.

As mentioned above, the inventors expect the smaller loop muteins (2- and 6-aa-loop muteins) to have lower biotin binding affinities. However, it is a surprise that both the 2- and 6-aa-loop muteins have the biotin binding affinities (10$^{-9}$M) that are also comparable to that of the W120A mutein. The only mutein with a lower biotin binding affinity (1.9×10$^{-8}$M) in this study is the 8-aa-loop-H127C mutein. Binding studies demonstrated that streptavidin muteins with a biotin binding affinity ($K_d$) in the range of 10$^{-9}$M would bind biotinylated molecules a little bit too tight (Data not shown). Only the 8-aa-loop-H127C mutein would be suitable for further characterization with the objective to develop affinity matrices for purification of biotinylated biomolecules. These characterizations are shown in the Examples below.

While it is envisioned that the aforementioned changes may be made in the wild-type sequence, other variation in non-critical regions of the molecule may be made. Such variation would typically be conservative substitutional mutations. Substitutional mutations involve the exchange of one amino acid for another at one or more sites within the protein, and may be designed to modulate one or more properties of the polypeptide, such as stability against proteolytic cleavage, without the loss of other functions or properties. Conservative substitutions, that is, one amino acid replaced with one of similar shape and charge, are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a peptide that defines that peptide's biological functional activity, certain amino acid substitutions can be made in a protein sequence, and its underlying DNA coding sequence, and nevertheless obtain a peptide with like properties. It is thus contemplated by the inventors that various changes may be made in the DNA sequences coding the peptide without appreciable loss of their biological utility or activity, as discussed below.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant peptide, which in turn defines the interaction of the peptide with other molecules.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine*−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of streptavidin muteins, but with altered and even improved characteristics.

The present invention may employ peptides that comprise modified, non-natural and/or unusual amino acids. A table of exemplary, but not limiting, modified, non-natural and/or unusual amino acids is provided herein below. Chemical synthesis may be employed to incorporated such amino acids into the peptides of interest.

TABLE 3

Modified, Non-Natural and Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

C. Purification of Proteins

It may be desirable to purify proteins according to the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein. The term "purified protein" as used herein, is intended to refer to a composition, isolatable from other components, wherein the protein is purified to any degree relative to its naturally-obtainable state. A purified protein therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. The clear example for the present invention is the use of biotin as the ligand.

2. Nucleic Acids

Important aspects of the present invention concern isolated DNA segments and recombinant vectors encoding streptavidin muteins and portions thereof, the creation and use of recombinant host cells through the application of DNA technology, that express steptavidin muteins. Sequences for steptavidin muteins nucleic acids include SEQ ID NOS:2, 4, 6, 8 and 10.

The present invention concerns DNA segments, isolatable from bacterial cells that are free from total genomic DNA and that encode steptavidin muteins. As used herein, the term "DNA segment" refers to a DNA molecule that has been isolated free of total genomic DNA of a particular species. Therefore, a DNA segment encoding steptavidin muteins refers to a DNA segment that is isolated away from, or purified free from, total mammalian genomic DNA. Included within the term "DNA segment" including DNA segments such recombinant vectors, including, for example, plasmids, cosmids, phage, viruses, and the like.

A. Variants

In particular embodiments, the invention concerns isolated DNA segments and recombinant vectors incorporating DNA sequences that encode steptavidin muteins. The term "bio-logically functional equivalent" is well understood in the art and is further defined in detail herein. Accordingly, nucleic acid sequences that have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 75% to about 99%, and more particularly about 81% and about 99% or about 86% to about 99%; or even more particularly, between about 91% and about 99%; of amino acids that are identical or functionally equivalent to the amino acids of, for example, SEQ ID NO:1, SEQ ID NO: 3, SEQ ID NO: 5, SEQ ID NO: 7, or SEQ ID NO: 9. In particular embodiments, the biological activity of a steptavidin muteins comprises stable low affinity binding to biotin, including reversible binding. "Stable low affinity binding" may include a dissociation constant ($K_D$) for biotin of the mutein in the range of $10^{-7}$ to $10^{-8}$M, and/or and an off-rate ($k_{off}$) for bound biotin in the streptavidin-biotin complex at about $10^{-4}$ $sec^{-1}$.

Another way of defining homology for nucleic acids is by hybridization conditions. For example, a nucleic acid will hybridize to sequences of greater or less homology based on the stringency of the hybridization conditions. For example, high stringency conditions may be exemplified by those includig approximately 10 mM Tris-HCl (pH 8.3), 50 mM KCl, 1.5 µM $MgCl_2$, at temperatures ranging from approximately 40° C. to about 72° C. A specific example of stringent hybridization conditions is overnight incubation at 42° C. in a solution comprising: 50% formamide, 5.times.SSC (150 mM NaCl, 15 mM trisodium citrate), 50 mM sodium phosphate (pH 7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., (1989), particularly Chapter 11 therein. Solution hybridization may also be used with the polynucleotide sequences provided by the invention.

It will also be understood that nucleic acid sequences may include those that encode additional residues, such as 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Obtaining Nucleic Acid Sequences

There are several methods available and well known to those skilled in the art to obtain DNAs encoding proteins. Sequences may be produced using PCR™ (or RT-PCR) (see U.S. Pat. Nos. 4,683,202, 5,928,906, each incorporated herein by reference). Alternatively the method of Rapid Amplification of cDNA ends (RACE) (see, for example, Frohman et al., 1988) may be used, including modifications of the technique, exemplified by the Marathon® technology (Clontech Laboratories Inc.). In Marathon®, cDNAs have been prepared from mRNA extracted from a chosen tissue and an 'adaptor' sequence ligated onto each end. PCR is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

4. Engineering Cells to Express Steptavidin Muteins

In certain embodiments, the present invention involves the production of streptavidin muteins. Such methods both rely upon expression constructs containing a streptavidin mutein coding region and the means for its expression, plus elements that permit replication of the constructs. Expression requires that appropriate signals be provided in the vectors, and which include various regulatory elements that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Vectors

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression.

B. Host Cells

While a variety of host cells can be used in accordance with the present invention, a particularly useful host cell is the bacterium *Bacillus subtilis*. Known also as the hay *bacillus* or grass *bacillus*, *B. subtilis* is a Gram-positive, catalase-positive bacterium commonly found in soil. A member of the genus *Bacillus*, *B. subtilis* is rod-shaped, and has the ability to form a tough, protective endospore, allowing the organism to tolerate extreme environmental conditions. Unlike several other well-known species, *B. subtilis* has historically been classified as an obligate aerobe, though recent research has demonstrated that this is not strictly correct.

*B. subtilis* is not a human pathogen. It may contaminate food but rarely causes food poisoning. *B. subtilis* produces the proteolytic enzyme subtilisin. *B. subtilis* spores can survive the extreme heat during cooking. It can divide symmetrically to make two daughter cells (binary fission), or asymmetrically, producing a single endospore that is resistant to environmental factors such as heat, acid, and salt, and which can persist in the environment for long periods of time. The endospore is formed at times of nutritional stress, allowing the organism to persist in the environment until conditions become favorable. Prior to the process to produce the spore the bacterium might become motile, through the production of flagella, and also take up DNA from the environment.

*B. subtilis* is a model organism used to study bacterial chromosome replication. Replication of the single circular chromosome initiates at a single locus, the origin (oriC). Replication proceeds bidirectionally and two replication forks progress in clockwise and counterclockwise directions along the chromosome. Chromosome replication is completed when the forks reach the terminus region, which is positioned opposite to the origin on the chromosome map. The terminus region contains several short DNA sequences (Ter sites) that promote replication arrest. Specific proteins mediate all the steps in DNA replication. Comparison between the proteins involved in chromosomal DNA replication in *B. subtilis* and in *Escherichia coli* reveals similarities and differences. Although the basic components promoting initiation, elongation, and termination of replication are well-conserved, some important differences can be found (such as one bacterium missing proteins essential in the other). These differences underline the diversity in the mechanisms and strategies that various bacterial species have adopted to carry out the duplication of their genomes.

*B. subtilis* has proven highly amenable to genetic manipulation, and has become widely adopted as a model organism for laboratory studies, especially of sporulation, which is a simplified example of cellular differentiation. It is also heavily flagellated, which gives *B. subtilis* the ability to move quite quickly. In terms of popularity as a laboratory model organism, *B. subtilis* is often used as the Gram-positive equivalent of *E. coli*.

5. Definitions

The word "about" means plus or minus 5% of the stated number.

As used herein, "affinity" refers to the dissociation constant ($K_d$) of a complex between a mutein or streptavidin, and biotin, as determined by standard methods known to those skilled in the art, an example of which is disclosed in the Examples herein. As is known in the art, $K_d$ is related to the association constant $K_a$, being the inverse thereof.

As used herein, "lower binding affinity" means a decrease in the binding affinity relative to streptavidin, which can be measured as an increase in $K_d$ or, alternatively, a decrease in $K_a$. The lower binding affinity can result from a change in one or both of $k_{on}$ (the "on rate," or "association rate constant," or $k_a$) and $k_{off}$ (the "off rate," or "dissociation rate constant," or $k_d$).

As used herein, "monomeric form" or "monomer" means a streptavidin or mutein subunit that is not in the form of a complex with another streptavidin or mutein subunit, or that does not form a complex with another streptavidin or mutein subunit.

As used herein, "tetrameric form" or "tetramer" means a protein complex that is comprised of four streptavidin and/or mutein subunits, and includes complexes in which one or more of the four subunits are different from one another.

As used herein, "subunit" means the protein that is generated from a streptavidin or mutein gene. "Subunit" is used interchangeably with "monomer."

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Construction of expression plasmids for production of streptavidin muteins in *B. subtilis*. Plasmid pSSAV (Wu et al., 2002) carrying a *B. subtilis* sacB signal peptide for secretion and a P43 promoter for transcription was used as the expression vector. This vector carries a synthetic gene for the wild-type full-length streptavidin. To construct the expression vectors to produce the loop muteins, the gene encoding the wild-type streptavidin in pSSAV was replaced by the PstI/BclI synthetic fragments encoding the loop muteins. The synthetic genes encoding loop muteins were ordered from Epoch Life Science, Inc. Texas, U.S.A. These synthetic genes were inserted in the *E. coli* pbluescript plasmid. Each *E. coli* plasmid was digested with PstI/BclI to release the synthetic gene fragment which would then be ligated to the PstI/BclI cut pSSAV to generate the expression vectors.

Production and affinity purification of streptavidin muteins. *Bacillus subtilis* cells carrying the expression vectors were cultivated in super-rich medium (Wu et al., 2002) at 30° C. for 9-12 hours. Culture supernatant was collected by centrifugation and streptavidin muteins were affinity purified using biotin-agarose as described previously (Wu and Wong, 2005a).

Other methods. BIAcore biosensor for determining the kinetic parameters, preparation of streptavidin-agarose matrix and purification of biotinylated proteins were performed as previously described (Wu and Wong, 2005a; Wu and Wong, 2005b).

Example 2

Results

Figure 4:
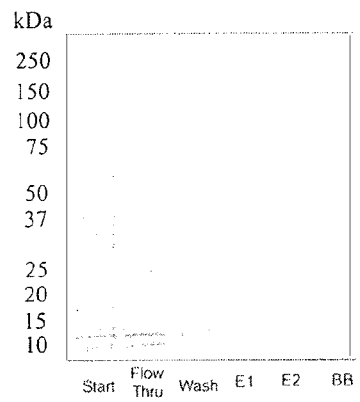
FIG. 4. Affinity purification of the 8-aa-loop-H127C mutein from the *B. subtilis* culture supernatant using the biotin-agarose matrix from ThermoFisher. "Start" shown in lane 1 is the culture supernatant before purification. BB is the protein sample from the boiled beads. E1 and E2 are the elution fractions.

Affinity purification of the 8-aa-loop H127C mutein. The 8-aa-loop-H127C mutein has an apparent molecular mass of 17 kDa which matches closely to the predicted molecular mass (16.3 kDa) for this protein (FIG. 4). It can bind to biotin-agarose and can be eluted off from the matrix by 4 mM biotin. Therefore, biotin-agarose can be used as an affinity matrix to purify this protein from the culture supernatant directly. The purified yield from 20 liters of *B. subtilis* culture supernatant in a fermentor is ~800 mg (i.e. ~40 mg/liter).

Figure 5:
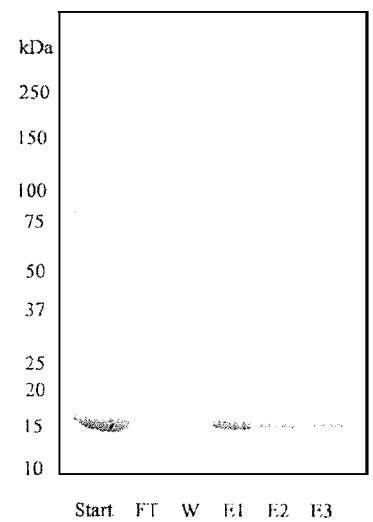
FIG. 5. Re-purification of purified 8-aa-loop-H127C mutein using a biotin-agarose column. The purified sample after dialysis to remove biotin was reapplied to the biotin-agarose column for another round of purification. "Start" is the purified 8-aa-loop-H127C mutein. FT: Flow-through fraction. W: wash fraction and E: elution fraction.

Bound biotin in the 8-aa-loop-H127C mutein can be removed by dialysis. Purified 8-aa-loop-H127C muteins eluted from the biotin agarose by 4 mM biotin will contain bound biotin. If biotin binding is reversible, bound biotin should be removable by dialysis. Indeed, the dialyzed 8-aa-loop-H127C muteins could rebind to the biotin-agarose column and could be eluted off from the column by 4 mM biotin in the elution buffer (FIG. 5). This illustrates that biotin binds to this protein in a reversible manner and can be removed by dialysis. Some 8-aa-loop-H127C mutein molecules could be observed in the flow-through fraction. This is probably because of overloading the column with excess muteins.

Stable subunit interactions in the 8-aa-loop-H127 mutein. The purified 8-aa-loop-H127C mutein can be immobilized to the agarose matrix with an estimated concentration of 3.8 mg/ml of settled agarose beads. Washing the 8-aa-loop-H127C mutein-agarose matrix with buffer did not elute any streptavidin subunits off from the column. Since it is likely that only one subunit in an tetrameric 8-aa-loop-H127C mutein was chemically coupled to the matrix (the other three subunits associated with the immobilized subunit via non-covalent interactions), this observation illustrates that the subunit interactions between the subunits in the tetrameric 8-aa-loop-H127C mutein were stable enough and the non-covalently associated subunits were not washed off from the column under the conditions used for the binding, washing and elution processes.

Figure 7:
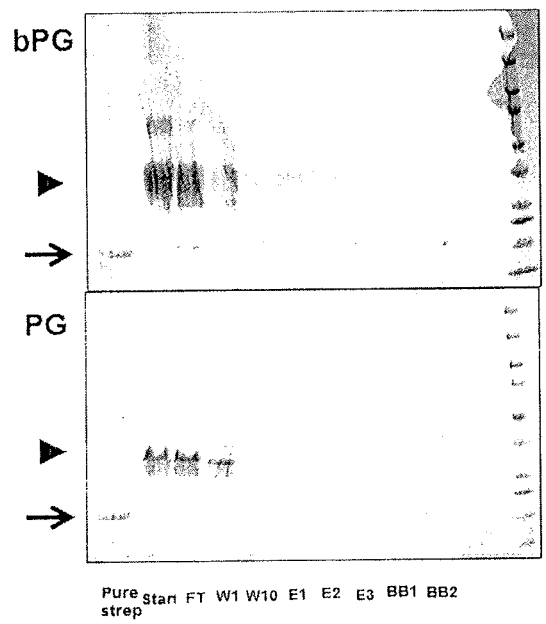
FIG. 7. Purification of biotinylated protein G using the 8-aa-loop-H127C mutein-agarose matrix. FT: flow-through fractions; W: wash fractions; E: elution fractions; BB: Boiled beads. Arrow head: biotinylated protein G in the upper panel and non-biotinylated protein G in the lower panel; Arrow: streptavidin. bPG: biotinylated protein G; PG: non-biotinylated protein G. The upper panel illustrates the successful purification of biotinylated protein G from the affinity matrix. In the lower panel, the non-biotinylated protein G serves as a negative control. The sample was loaded to the same affinity matrix and no significant non-specific interaction between non-biotinylated protein G and the matrix could be observed.
Figure 8:
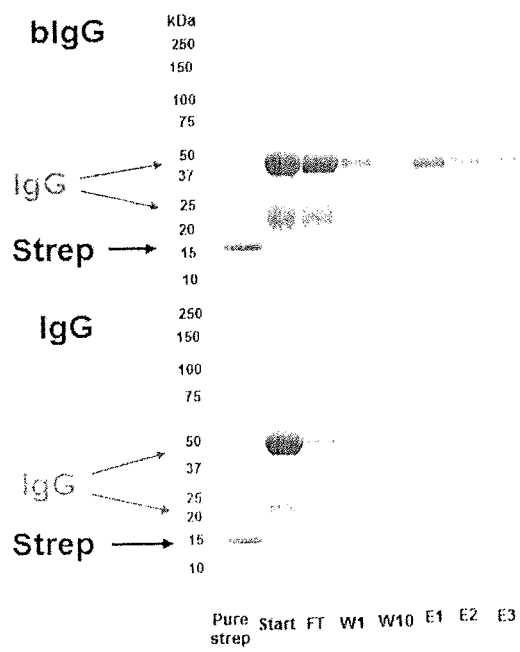
FIG. 8. Purification of biotinylated IgG using the 8-aa-loop-H127C agarose. The 50- and 24-kDa protein bands are the heavy and light chains of IgG, respectively. Upper panel shows the purification of the biotinylated IgG. Lower panel shows the loading of the non-biotinylated IgG sample.

Application of the 8-aa-loop-H127C mutein-agarose matrices for purification of biotinylated protein G and biotinylated IgG. The 8-aa-loop-H127C mutein-agarose matricies can be applied successfully to purify chemically biotinylated protein G and IgG. The bound biotinylated proteins could be eluted off from the column using 4 mM biotin (FIGS. 7 and 8).

Reusability of the 8-aa-loop-H127C mutein-agarose. The 8-aa-loop-H127C mutein-agarose matrix can be reused for 6 times without any significant loss in binding capacity (data not shown).

Figure 9:
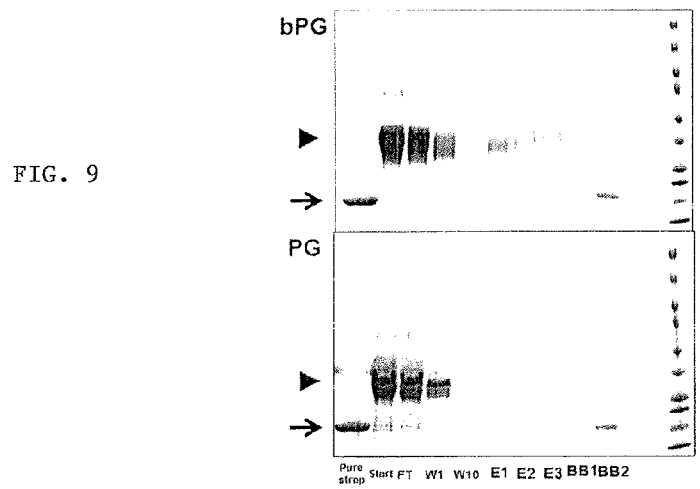
FIG. 9. Purification of biotinylated protein G using a monomeric avidin-agarose column. BB1 and BB2 represent proteins from the boiled bead fractions. Arrow: monomeric streptavidin; Arrow head: biotinylated protein G in the upper panel and non-biotinylated protein G in the lower panel.

8-aa-loop-H127C mutein vs monomeric avidin. The 8-aa-loop-H127C mutein-agarose matrix offers better performance than the monomeric avidin matrix in purifying biotinylated proteins. Biotinylated protein G could be eluted off from the 8-aa-loop-H127C mutein-agarose matrix efficiently (FIG. 7). No significant amounts of biotinylated protein G were retained in the column (Lanes BB1/2 in FIG. 7). In contrast, some biotinylated protein G molecules were still retained in the monomeric avidin matrix after elution (FIG. 9, see lanes BB1 and BB2). Presence of certain levels of biotinylated protein G in the BB1 and BB2 fractions is not a surprise since monomeric avidin matrix is known to have some tetrameric form of avidin molecules present. These tetrameric avidin molecules have a high affinity to bind biotinylated molecules in an irreversible manner with a $K_d$ of $10^{-15}$ M.

8-aa-loop-H127C mutein vs Roche streptavidin mutein. Currently, a streptavidin mutein with reversible biotin binding ability is commercially available from Roche (U.S. Pat. No. 6,312,916 B1). This mutein has three changes in its protein sequence (S27R, S45R and L110W). The biotin binding affinity ($1.3 \times 10^{-7}$ M) of the Roche SAV mutein is ~10 fold lower than that ($1.9 \times 10^{-8}$ M) of the 8-aa-loop-H127C mutein. The half-life (1.9 min) of biotin in the SAV-biotin complex for the Roche mutein is also ~14 fold shorter than that (27 min) of the 8-aa-loop-H127C mutein. Interestingly, as shown in FIG. 10, the binding capacity of the Roche SAV mutein matrix is not as high as that of the 8-aa-loop-H127C mutein matrix.

Figure 10:
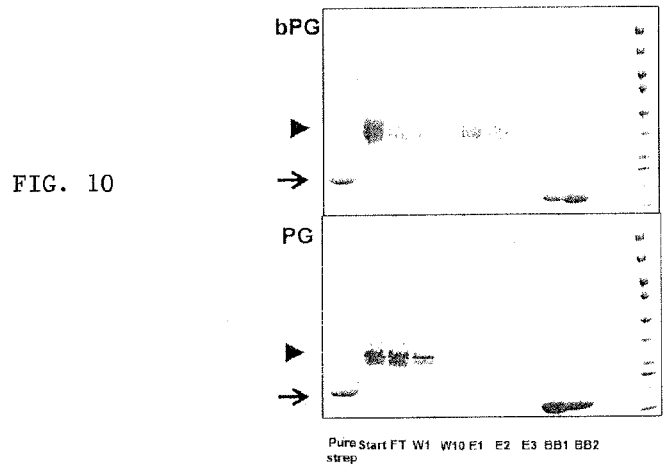
FIG. 10. Purification of biotinylated protein G using the Roche streptavidin mutein matrix. FT is the flow through fraction. BB1 and BB2 are the boiled bead fractions. Arrow head: biotinylated protein G in the upper panel and non-biotinylated protein G in the lower panel; Arrow: streptavidin.

Comparing the upper panel in both FIGS. 7 and 10, the Roche matrix seemed to be able to capture more biotinylated protein G. However, the streptavidin band intensities in the BB1 and BB2 fractions in FIG. 10 illustrate that the amounts of the Roche streptavidin mutein immobilized to the matrix were at least 10 times more than that (BB1 and BB2 fractions in FIG. 7) of the 8-aa-loop-H127C mutein in the matrix. If the amount of immobilized streptavidin in the matrix was normalized, the matrix with the 8-aa-loop-H127C mutein had a much better binding capacity than the matrix with the Roche streptavidin mutein.

The H127C mutation in the 8-aa-loop-H127C mutein may not be important. The H127C mutation in the 8-aa-loop-H127C mutein is likely not an essential mutation and can be eliminated without affecting the desirable properties observed in the 8-aa-loop-H127C mutein.

Figure 11:
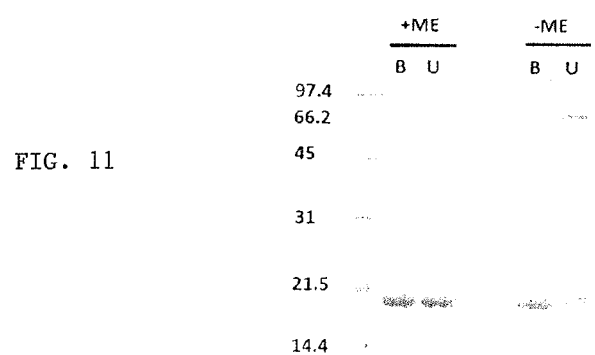
FIG. 11. SDS-PAGE analysis of 8-aa-loop-H127C mutein in the presence of 4 mM biotin under the conditions with and without mercaptoethanol (ME). U and B indicate the samples were unboiled and boiled, respectively, before loading.

As above-mentioned, the 4-aa-loop mutein immobilized to the matrix tended to dissociate during the elution step. The inventors were concerned that the 8-aa-loop mutein might have the same problem. Therefore, the H127C mutation was introduced in the structural gene encoding the 8-aa-loop mutein to generate the 8-aa-loop-H127C mutein. Subunit A is expected to form a disulfide bond with subunit C and subunit B should form a disulfide bond with subunit D. If these disulfide bonds are formed, one would expect to see the presence of the disulfide bonded dimeric structures (subunits A-C and subunits B-D) in the SDS-PAG when the samples were prepared in the sample application buffer without the supplement of reducing agent (i.e., mercaptoethanol) and the samples were boiled before loading. However, under this condition, only small amounts of tetrameric SAV but no dimeric streptavidin could be observed (FIG. 11, lane 5). Several rounds of independent analyses indicated that the amount of disulfide bonded dimeric streptavidin subunits might represent 10% or less of the total streptavidin population. Therefore, the data reflected no significant disulfide bond formation in the 8-aa-loop-H127C mutein.

Figure 6:
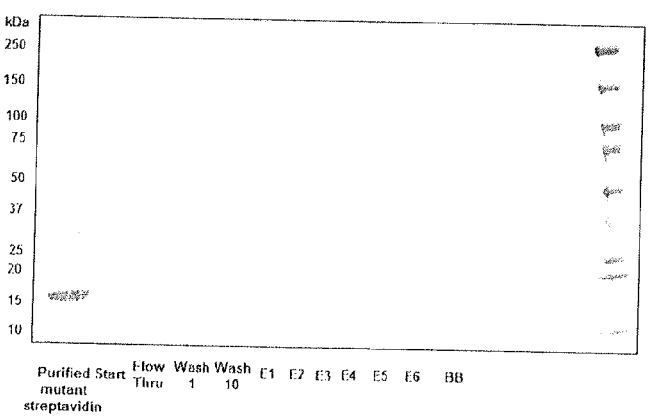
FIG. 6. Immobilized 8-aa-loop-H127C muteins are stable and are not washed off from the matrix under the binding, washing and elution conditions. The boiled bead (BB) fragment shows the amount of streptavidin immobilized to the beads.

Since the immobilized tetrameric 8-aa-loop-H127C mutein in the agarose matrix is stable enough to survive the washing and elution conditions without releasing any non-covalently associated streptavidin subunits as shown in FIG. 6, it suggests that the H127C mutation is not needed in this mutein.

Possible explanations for the lower biotin binding affinity in the 8-aa-loop-H127C mutein. The three dimensional structure of the 8-aa-loop-H127C mutein in complex with biotin was determined by X-ray crystallography to high resolution (1.95 Å). In this structure, the 8-aa-loop-H127C mutein is in the tetrameric state. There are two significant findings.

Figure 12:
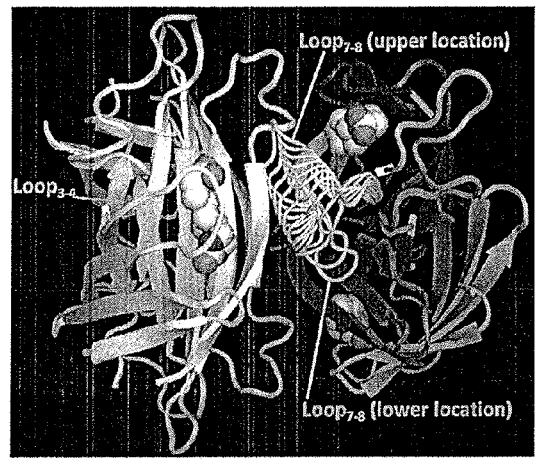
FIG. 12. Modeling of the mobile engineered loop$_{7-8}$ in the subunit of the 8-aa-loop-H127C streptavidin. This loop is modeled in 10 different positions to illustrate that this loop can function as a dynamic gateway in the subunit for the exit of the bound biotin. Loop$_{3-4}$ in the subunit is in the closed conformation. The loop (loop$_{7-8}$) in the upper position will form a wall as part of the biotin binding pocket for the subunit. This gate is in the closed state. When the loop (loop$_{7-8}$) is in the lower position, the gate is in the open state.

The engineered loop is mobile. The entire engineered loop (DSSNGSDG) in the 8-aa-loop-H127C mutein is not visible. This indicates that this region is highly mobile and can function as a second door in streptavidin to allow a bound biotin to escape from the biotin binding pocket even the first door formed by $loop_{3-4}$ is in the closed state. Absence of Trp-120 weakens the interaction between biotin and the biotin binding pocket. Dynamic movement of the engineered loop allows the release of biotin from the biotin binding pocket. Although the engineered loop is not visible in the mutein, it is possible to model the feasible locations of these loops based on the possible loop conformations available from the PDB databank. The purpose of this modeling is to illustrate the concept that this engineered loop can function as a dynamic door in the closed and open states (FIG. 12). These models are just for illustration purpose.

Figure 13:
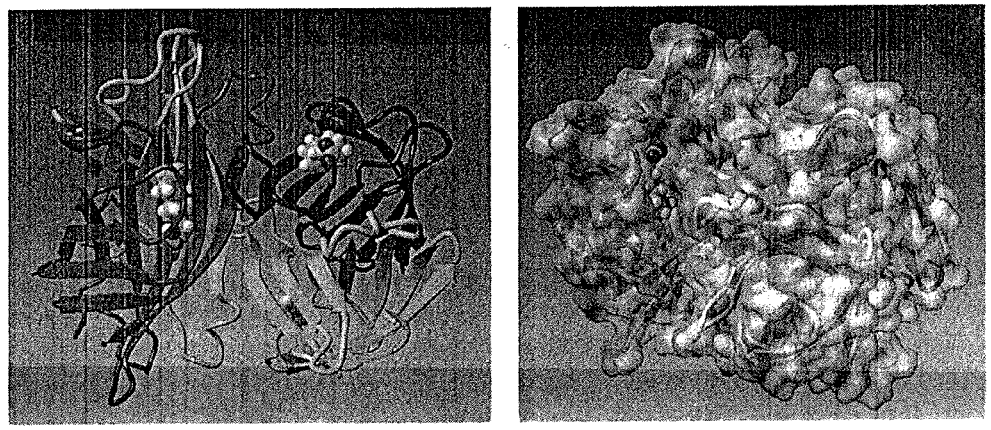
FIG. 13. Modeled loop$_{7-8}$ in the 8-aa-loop-H127C mutein is in the upper position and this biotin exit gate is in the closed state.
Figure 14:
FIG. 14. Modeled loop$_{7-8}$ in 8-aa-loop-H127C mutein is in the lower position and this biotin exit gate is in the open state.
Figure 15:
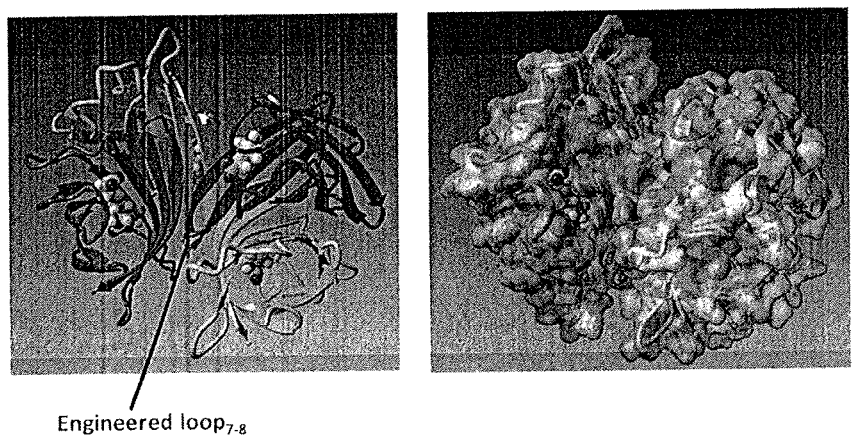
FIG. 15. Homology modeled structure of the 2-aa-loop mutein.

In the closed conformation (when the $loop_{7-8}$ is in the upper position) shown in FIG. 13, there is a very narrow opening between subunits and biotin would not be able to escape from this structure. In contrast, when the engineered $loop_{7-8}$ is in the open state, it is possible to have a big opening available which allows biotin to escape from this biotin binding pocket (FIG. 14).

A change of the relative orientation of subunits in the 8-aa-loop-H127C mutein. When the structure of tetrameric 8aa-loop-H127C mutein was superimposed to the structure of wild-type streptavidin, two subunits in the 8-aa-loop-H127C structure could superimpose relatively well with the corresponding subunits in the structure of wild-type streptavidin (1SWE). However, there other two subunits (subunits A and B) did not superimpose that well. There is a 9.98° rotation between the A subunit in the mutein and the A subunit in wild-type streptavidin. The same is true for the B subunits in these structures.

This observation was unexpected at the time when the inventors designed this mutein. Such a 9.98° rotation was not observed in the structures of streptavidin (pdb files: 1SWE, 2IZF, 1HXL, 2RTP, 2RTF) and the streptavidin muteins (3MG5, 1SWG, 2Y3F, 1SWR) which were selected for analysis. These muteins included both the W120A mutein (pdb file: 1SWR) and traptavidin (pdb file: 2Y3F) (Chivers et al., 2011). It is vital to note that a single mutation of W120 to alanine is not sufficient to allow rotation to occur between subunits in the tetrameric streptavidin. Since residues in $loop_{7-8}$ from one subunit in tetrameric streptavidin interact with many residues in two neighboring subunits, these interactions can fix the relative orientation of a subunit in the tetrameric structure. Replacement of residues in $loop_{7-8}$ in the 8-aa-loop-H127C mutein weakens these interactions. Consequently, $loop_{7-8}$ becomes flexible and subunits A and B can have a different relative orientation with subunits C and D.

Example 3

Discussion

Replacement of residues in loop$_{7-8}$ of the wild-type streptavidin results in allowing loop$_{7-8}$ to become flexible and changing the relative orientation of subunits in the tetrameric structure. These structural changes lead to lowering of the biotin binding affinity in the 8-aa-loop-H127C mutein. The strength of biotin interaction with streptavidin was analyzed using the ligand energy inspector function in the Molegro molecular viewer program (Thomsen and Christensen, 2006). The free binding energy can be reflected by the MolDock scores as shown in Table 4. The more the negative value indicates the stronger interaction. This study suggests the lower biotin binding affinity in the 8-aa-loop-H127C mutein is mainly contributed by both the absence of interactions (i.e., W120 (not present in the mutein) and Lys 121) and weaker interactions between biotin and residues in the biotin binding pocket. In reference to the wild-type streptavidin, a few residues in the 8-aa-loop-H127C mutein have a little bit stronger interactions with biotin (data not shown). However, the net outcome is that the 8-aa-loop-H127C mutein has a weaker biotin binding affinity.

TABLE 4

Interaction of biotin with residues in the biotin binding pocket of subunit A

| Protein | 8-aa-loop | Wild-type SAV (2IZF) | Difference (wild-type − mutein) |
|---|---|---|---|
| MolDock score | −125.6 | −140.1 | −14.4 |
| Trp 120 (from subunit D) | 0 | −10.5 | −10.5 |
| Lys 121 (from subunit D) | 0 | −1.3 | −1.3 |
| Asp128 | −4.4 | −7.7 | −3.3 |
| Ser 45 | −6.6 | −8.0 | −1.4 |
| Asn 23 | −4.1 | −5.2 | −1.1 |
| Leu 25 | −3.5 | −4.3 | −0.8 |

With weaker binding of biotin in the 8-aa-loop-H127C mutein, the bound biotin is expected to have higher frequency to detach from the binding site. Whether the detached biotin will escape successfully from streptavidin or be trapped and recaptured in the biotin binding pocket again will depend on the flexibility of $loop_{3-4}$ and $loop_{7-8}$. In the wild-type streptavidin, $loop_{7-8}$ is not mobile. $Loop_{3-4}$ is unlikely to have a high degree of mobility in the presence of biotin since many residues in this loop can interact with the bound biotin. In contrast, mobility in the engineered loop can create a new exit pathway for the release of biotin from the biotin binding pocket in the engineered streptavidin. This new exit pathway does not exist in both the wild-type and W120A streptavidin since $loop_{7-8}$ forms a rigid structure in these proteins.

During this study, a new form of genetically modified streptavidin termed traptavidin has been reported (Chivers et al., 2010). The bound biotin dissociates from traptavidin at least 10 times slower than from the wild-type streptavidin. X-ray crystallographic study (Chivers et al., 2011) of the structure of traptavidin indicates that $loop_{3-4}$ is non-mobile in this structure and has adopted a closed conformation no matter in the presence or absence of biotin. Interestingly, analysis of the biotin binding strength of traptavidin using the Molegro molecular viewer indicates that the MolDoc score (−139.3) of traptavidin is comparable to that (−140.1) of the wild-type streptavidin. This observation suggests that the loop flexibility and mobility not reflected from the interaction strength study by Molegro molecular viewer can significantly affect the biotin binding affinity. In this case, flexibility and mobility of $loop_{7-8}$ in the 8-aa-loop-H127C mutein can facilitate the escape of the bound biotin from the biotin binding pocket. This effect can contribute to lowering the biotin binding affinity.

In the entire series of Trp-120 loop streptavidin muteins, most of them (ΔWHC, 2- and 6-aa-loop muteins) have the biotin binding affinity similar to that of the W120A mutein in the range of $10^{-9}$ M. Only the 8-aa-loop H127C mutein has the desirable properties for reversible biotin binding capability that is suitable for the development of affinity matrix for purification of biotinylated biomolecules. Kinetic studies indicated that both the 2- and 6-aa loop muteins have lower off rate in comparison with that from the 8-aa-loop mutein (Table 2). This outcome is somewhat unexpected. Based on the theoretical predictions, the 2- and 6-aa-loop muteins are expected to have lower biotin binding affinity (i.e., $K_d > 10^{-9}$ M) than that of the W120A mutein. In the homology modeled structure (FIG. 15), the two amino acids in the engineered $loop_{7-8}$ are just long enough to link strands 7 and 8 together in the 2-aa-loop mutein. There is a big opening present in each biotin binding pocket to allow the escape of the bound biotin. This should be equivalent to have a back door open all the time. Biotin dissociated from the biotin binding site should be able to escape easily from the biotin binding pocket.

In the case for the 6-aa-loop mutein, the engineered loop may not be big enough to form a wall in the biotin binding pocket to prevent the escape of the bound biotin. Furthermore, the engineered 6-amino-acid loop is expected to be mobile. Therefore, both the 2- and 6-aa-loop muteins are expected to have the $K_d$ values for biotin to be $>10^{-9}$ M (e.g., $10^{-8}$M or $10^{-7}$M). However, this is not the case. Of course, homology modeling cannot predict the degree of flexibility of the engineered loop and the presence of certain rotation between subunits in these engineered muteins. Most importantly, the actual three dimensional structures for these muteins have not been determined. The homology modeled structures may not reflect the actual structures. It is possible that a combination of several factors including elimination of W120, loop mobility and rotations between subunits in the 8-aa-loop-H127C mutein is needed to account for the desirable kinetic properties observed in the 8-aa-loop-H127C mutein.

To purify biotinylated molecules, two matrices are commercially available. The first one is the monomeric avidin matrix. Avidin has a structure similar to streptavidin and is also tetrameric in nature. The traditional way to prepare the monomeric avidin matrix requires chemical coupling of a subunit of the tetrameric avidin to the matrix. The matrix is then treated with denaturing agents so that the other three subunits that are not covalently coupled to the matrix will be stripped off from the matrix. The immobilized monomeric avidin in the matrix has subsequently to be renatured. This approach has three drawbacks. First, one has to sacrifice three avidin subunits for each avidin subunit immobilized to the matrix. Therefore, the production cost is relatively high. Second, subunits of avidin associate together to form tetrameric structures. These subunits mainly interact with each other via hydrophobic interactions. Monomeric avidin will expose a large hydrophobic surface. This may result in non-specific interactions with proteins in the crude extract. Third, it is difficult to completely denature the tetrameric avidin because of the strong subunit interactions. Incomplete denaturation of avidin results in the presence of some tetrameric avidin in the matrix. These tetrameric avidin molecules can bind biotinylated molecules irreversibly. Combination of the second and third factors mentioned above can potentially account for the presence of higher levels of bound biotinylated molecules in the matrices that cannot be eluted off from the column (FIG. 9, BB1 and BB2). The use of the 8-aa-loop H127C mutein produced from B. subtilis via recombinant DNA method can address all three concerns.

The second commercially available matrix is the Roche streptavidin mutein. By comparing FIGS. 7 and 10, the binding capacity of the Roche streptavidin mutein seems to be significantly less than that of the 8-aa-loop-H127C mutein. Therefore, the engineered 8-aa-loop-H127C mutein has its advantages over the currently available matrices for affinity purification of biotinylated molecules. In fact, the 8-aa-loop-H127C mutein has all the desirable features listed in the objective section. This makes the 8-aa-loop-H127C mutein a useful agent for various biotechnological applications.

\* \* \*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,554,101
U.S. Pat. No. 4,683,202
U.S. Pat. No. 5,928,906
U.S. Pat. No. 6,312,916 B1
Ausubel et al., Current Protocols in Molecular Biology, Greene Publishing Associates and Wiley Interscience, N.Y., 1994.
Capaldi et al., Biochem. Biophys. Res. Comm., 74(2):425-433, 1977.
Chilkoti et al., Proc. Natl. Acad. Sci. USA, 92:1754-1758, 1995.
Chivers et al., Biochem. J., 435(1):55-63, 2011.
Chivers et al., Nat. Methods, 7(5):391-393, 2010.
Freitag et al., J. Mol. Biol., 279(1): 211-221, 1998.
Freitag et al., Protein Sci., 6(6):1157-1166, 1997.
Frohman et al., Proc. Natl. Acad. Sci. USA, 85:8998-9002, 1988.
Johnson et al., In: Biotechnology And Pharmacy, Pezzuto et al. (Eds.), Chapman and Hall, NY, 1993.
Kohanski and Lane, Methods Enzymol., 184:194-200, 1990.
Kyte and Doolittle, J. Mol. Biol., 157(1):105-132, 1982.
Qureshi et al., J. Biol. Chem., 276(49):46422-46428, 2001.
Reznik et al., Nat. Biotechnol., 14(8):1007-1011, 1996.
Sambrook, et al., Molecular Cloning: A Laboratory Manual, $2^{nd}$ Ed., Cold Spring Harbor, N.Y., 1989.
Thomsen and Christensen, J. Med. Chem., 49(11): 3315-3321, 2006.
Wilchek and Bayer, Methods Enzymol., 184: 5-13, 1990.
Wu and Wong, J. Biol. Chem., 280(24): 23225-23231, 2005a.
Wu and Wong, Protein Expr. Purif., 46(2): 268-273, 2005b.
Wu et al., Protein Expr. Purif., 24(3): 348-356, 2002.

What is claimed is:

1. A streptavidin mutein comprising the sequence Asp-Ser-Ser-Asn-Gly-Ser-Asp-Gly (SEQ ID NO: 11) at positions 114-121 corresponding to full-length wild-type streptavidin (SEQ ID NO:1).

2. The mutein of claim 1, further comprising $Cys_{127}$.

3. The mutein of claim 1, wherein said mutein comprises SEQ ID NO:3.

4. The mutein of claim 1, wherein said mutein comprises SEQ ID NO: 9.

5. The mutein of claim 1, wherein said mutein comprises SEQ ID NO:5.

6. The mutein of claim 1, wherein said mutein comprises SEQ ID NO:7.

7. A nucleic acid encoding a streptavidin mutein comprising the sequence Asp-Ser-Ser-Asn-Gly-Ser-Asp-Gly (SEQ ID NO: 11) at positions 114-121 corresponding to full-length wild-type streptavidin (SEQ ID NO:1).

8. The nucleic acid of claim 7, wherein said nucleic acid encodes a mutein comprising $Cys_{127}$.

9. The nucleic acid of claim 7, wherein said nucleic acid encodes a mutein comprising SEQ ID NO:3.

10. The nucleic acid of claim 7, wherein said nucleic acid encodes a mutein comprising SEQ ID NO: 9.

11. The nucleic acid of claim 7, wherein said nucleic acid encodes a mutein comprising SEQ ID NO:5.

12. The nucleic acid of claim 7, wherein said nucleic acid encodes a mutein comprising SEQ ID NO:7.

13. A streptavidin mutein complex comprising two to four streptavidin mutein subunits comprising the sequence Asp-Ser-Ser-Asn-Gly-Ser-Asp-Gly (SEQ ID NO:11) at positions 114-121 corresponding to full-length wild-type streptavidin (SEQ ID NO:1).

14. The complex of claim 13, wherein said complex further comprises a bound biotin molecule.

15. The complex of claim 13, wherein said complex further comprises two, three or four bound biotin molecules.

16. A method of binding a biotin molecule comprising contacting a biotin molecule with a streptavidin mutein complex comprising two to four streptavidin mutein subunits comprising the sequence Asp-Ser-Ser-Asn-Gly-Ser-Asp-Gly (SEQ ID NO:11) at positions 114-121 corresponding to full-length wild-type streptavidin (SEQ ID NO:1).

17. The method of claim 16, wherein said biotin molecule is bound to a matrix.

18. The method of claim 17, wherein said matrix is a porous or nonporous particle, a membrane, a monolithic support, or a natural or synthetic polymer.

19. The method of claim 16, wherein said biotin molecule is bound to a free molecule.

20. The method of claim 19, wherein said free molecule is a protein, a glycoprotein, a peptide, an oligonucleotide, a polynucleotide, a carbohydrate, a lipid, a glycolipid, an organic chemical, a synthetic polymer, an organo-metal chelate, a fluorescent molecule, a microparticle, a nanoparticles, or a drug, or a combination of any of the foregoing.

21. The method of claim 16, further comprising the step of reversing the binding of said biotin molecule and said complex.

22. A method of purifying a target molecule comprising:
(a) providing a streptavidin mutein complex comprising two to four streptavidin mutein subuntis comprising the sequence Asp-Ser-Ser-Asn-Gly-Ser-Asp-Gly (SEQ ID NO:11) at positions 114-121 corresponding to full-length wild-type streptavidin (SEQ ID NO:1), wherein said streptavidin mutein complex is immobilized to a matrix;
(b) contacting a target molecule/biotin molecule complex with said streptavidin mutein complex on said matrix; and
(c) washing said matrix to remove non-specifically bound material.

23. The method of claim 22, further comprising (d) eluting bound target molecule/biotinylated molecule complex from said matrix.

24. The method of claim 22, wherein said target molecule is a protein, a glycoprotein, a peptide, an oligonucleotide, a polynucleotide, a carbohydrate, a lipid, a glycolipid, an organic chemical, a synthetic polymer, an organo-metal chelate, a fluorescent molecule, a microparticle, a nanoparticles, or a drug, or a combination of any of the foregoing.

25. The method of claim 22, wherein said matrix is a porous or nonporous particle, a membrane, a monolithic support, or a natural or synthetic polymer.

* * * * *